United States Patent [19]

Noda et al.

[11] Patent Number: 4,734,445
[45] Date of Patent: Mar. 29, 1988

[54] LATEX COMPOSITIONS CAPABLE OF PRODUCING ELASTOMERS WITH HYDROPHILIC SURFACES

[75] Inventors: Isao Noda, Cincinnati; Douglas F. Hager, West Chester, both of Ohio

[73] Assignee: The Procter & Gamble Company, Cincinnati, Ohio

[21] Appl. No.: 943,988

[22] Filed: Dec. 18, 1986

[51] Int. Cl.$^4$ .............................. C08F 83/00; B05C 1/16
[52] U.S. Cl. .................................... 523/201; 523/111; 525/902; 428/137
[58] Field of Search ............... 523/201; 525/902; 428/137; 523/111

[56] References Cited

U.S. PATENT DOCUMENTS

| 3,397,165 | 8/1968 | Goodman et al. | 260/29.7 |
|---|---|---|---|
| 3,575,913 | 4/1971 | Meier | 260/29.7 |
| 3,580,880 | 5/1971 | Clarke et al. | 260/29.6 |
| 3,978,160 | 8/1976 | Seiler et al. | 260/874 |
| 4,026,962 | 5/1977 | Lambia et al. | 260/827 |
| 4,058,124 | 11/1977 | Yen et al. | 523/111 |
| 4,279,798 | 7/1981 | Aggarwal et al. | 260/33.4 |
| 4,324,246 | 4/1982 | Mullane et al. | 128/287 |
| 4,325,856 | 4/1982 | Ishikawa et al. | 521/458 |
| 4,385,164 | 5/1983 | Sinclair et al. | 526/201 |
| 4,567,099 | 1/1986 | Van Gilder et al. | 523/201 |

Primary Examiner—Joseph L. Schofer
Assistant Examiner—Peter D. Mulcahy
Attorney, Agent, or Firm—Jerry J. Yetter; Steven J. Goldstein; Eric W. Guttage

[57] ABSTRACT

Latex compositions suitable for applications requiring surface hydrophilicity are disclosed. The latexes can be used in liquid film-forming compositions which comprise: (1) a liquid phase such as water, water-miscible solvents and mixtures thereof; and (2) latex particles dispersed in the liquid phase. The particles comprise an elastomeric hydrophobic core with a hydrophilic "shell" which is integral with the core. When the liquid phase is removed, the particles are capable of forming an elastomeric film having a substantially permanent hydrophilic surface.

2 Claims, No Drawings

LATEX COMPOSITIONS CAPABLE OF PRODUCING ELASTOMERS WITH HYDROPHILIC SURFACES

TECHNICAL FIELD

The present application relates to latex compositions which provide surface-hydrophilic coatings and films.

Materials which have hydrophilic surfaces are easily wetted by water and other polar liquids. This should be contrasted with bulk hydrophilicity where the material "swells" in the presence of these polar liquids. Materials without bulk hydrophilicity having only surface hydrophilicity do not swell and thus can be highly desirable where "wet strength" is required. Materials which are bulk hydrophilic often have decreased wet strength when swollen with water.

For many product applications the hydrophilic surface needs to have some degree of permanency. Basically, this translates into the ability of the surface to maintain wettability after repeated exposures to water or other polar liquids, as well as exposure to air. Permanency of the hydrophilic surface can be particularly difficult to achieve where the underlying bulk material is hydrophobic, such as in the case of polyethylene or polypropylene films. In these instances, the hydrophilic surface layer needs to be compatible and adherent to the underlying bulk material; otherwise, the hydrophilic surface can be stripped away after relatively few exposures to water or other polar liquids. In addition, when the underlying bulk material is soft or elastomeric, the surface layer can be "swallowed up", resulting in a loss of surface hydrophilicity.

Surface hydrophilicity is preferably combined with other properties such as flexibility, elasticity and strength. One category of materials desirably having such combined properties includes the binder systems used in making nonwoven fabrics and paper products. A variety of latex compositions have previously been used as binders, including acrylic (methacrylic) latexes and styrene-butadiene latexes. These latexes are typically formed by emulsion polymerization of the respective monomers and can optionally contain surfactants to stabilize the latex particles, as well as to impart a certain amount of hydrophilicity to the non-woven product. These prior art latex binder systems tend to be non-wettable (hydrophobic) or to lose their wettability after repeated exposure to water. Additionally, the mechanical strength of these binders can very greatly depending on changes in pH.

Water-soluble cationic wet strength resins have also been used as binders in the formation of nonwoven paper products. These resins undergo a chemical reaction to form covalent bonds with the cellulosic fibers, as well as a cross-linking reaction which makes them water-insoluble. Wet-strength resins tend to form hard (non-elastic) bonds between fibers which can increase the stiffness of the paper. These resins are also not completely resistant to water, which can change the mechanical strength of the bonds between the fibers.

Accordingly, it would be desirable to develop materials which can: (1) impart surface hydrophilicity to bulk materials, in particular those which are hydrophobic and/or elastomeric, with some degree of permanency; and (2) provide a combination of properties such as flexibility, elasticity and strength, in addition to surface hydrophilicity. It would also be desirable to have materials which can be coated onto hydrophobic surfaces such as polymer or sheet films to render the surfaces selectively hydrophilic.

BACKGROUND ART

A. Polybutadiene-polyethylene oxide (PBD-PEO) diblock co-oligomers

U.S. Pat. No. 4,279,798 to Aggerwal et al., discloses PBD-PEO block copolymers of low molecular weight, e.g. 4000 M.W. The diblock is formed by preparing a hydroxy terminated polybutadiene prepolymer using an organo-lithium initiator, with subsequent addition of ethylene oxide using a double metal cyanide catalyst. These PBD-PEO diblocks are disclosed to be useful as dispersants for crude oil/alcohol mixtures. See also U.S. Pat. No. 3,978,160 to Seiler et al, issued Aug. 31, 1976, which discloses low molecular weight PBD-PEO diblocks (e.g. 3600 M.W.) suitable as anti-static agents, emulsifiers, surfactants and finishing agents for paper and textiles.

B. Aqueous polymer dispersions prepared using amphiphilic diblock copolymers

U.S. Pat. No. 4,385,164 to Sinclair et al., issued May 24, 1983, discloses aqueous dispersion polymerization of an unsaturated monomer such as butadiene in the presence of a block copolymer dispersion stabilizer. The stabilizer comprises 50-97% of a hydrophilic block (e.g. polyethylene oxide) and 3-50% of a hydrophobic block (e.g. polystyrene) having pendant functional groups (e.g. vinyl) capable of reacting with the monomer that is polymerized. The copolymer can have a weight average M.W. of from 1000 to $10^6$ with the hydrophilic block preferably having an M.W. of at least 4000, and the hydrophobic block preferably having an M.W. of at least 10,000. A free-radical initiator which is soluble in the monomer is used to catalyze the dispersion polymerization. The polymers formed can be used for coating and impregnating various substrates such as textiles, fabrics, paper, etc. Example 4 discloses the aqueous dispersion polymerization of butadiene to provide small polymeric spheres using a copolymer comprising 85% of a methoxy poly(ethylene oxide)-methylacrylate hydrophilic block and 15% of a t-butyl polystyrene hydrophobic block having pendant epoxy functional groups. This block copolymer had a number average M.W. of 10,460 and a weight average M.W. of 13,930.

C. Dispersion polymerization using amphiphilic diblock copolymers

U.S. Pat. No. 4,026,962 to Lambia et al., issued May 31, 1977, discloses a process for dispersion-polymerization of vinyl monomers (e.g., styrene) in water using a block copolymer of the A-B type wherein A represents a hydrophobic block and B represents a hydrophilic block. Suitable block copolymers include polystyrene-quaternized poly-(vinyl-2-pyridine), polystyrene-quaternized poly(vinyl-4-pyridine), and polyisoprene-quaternized poly(vinyl-4-pyridine). This process provides beads or balls of the desired polymer having very regular size distribution. See also U.S. Pat. No. 3,580,880 to Clarke, issued May 25, 1971, which discloses stable dispersions of polymer particles prepared by polymerizing an olefin type monomer in a liquid (e.g., water) in the presence of an amphipatic stabilizer which associates with and stabilizes the dispersion of polymer particles formed.

D. Aqueous latexes formed by emulsion polymerization using a seed latex

U.S. Pat. No. 3,397,165 to Goodman et al., issued Aug. 13, 1968, discloses the preparation of butadiene polymer latexes useful as paper impregnants or for coating surfaces. These latexes are formed by providing a butadiene/styrene copolymer seed and then polymerizing butadiene and styrene monomers together with acrylic or methacrylic acid.

E. Aqueous latexes formed by emulsion polymerization using "shot growth" technique U.S. Pat. No. 3,575,913 to Meier, issued Apr. 20, 1971, discloses a latex especially adapted for paper coating. This latex is formed by polymerizing a monomeric composition containing an unsaturated dicarboxylic acid (itacanoic acid), a vinyl aromatic (styrene), and a conjugated diene (butadiene). After at least 90% of the monomeric composition is polymerized, 1-5% of an acrylic acid monomer is added and then polymerization is continued.

SUMMARY OF THE INVENTION

The present invention encompasses latex compositions, which comprise:
(1) a liquid phase selected from the group consisting of water, water-miscible solvents and mixtures thereof;
(2) latex particles dispersed in said liquid phase, said particles comprising an elastomeric hydrophobic core and an outer hydrophilic shell integral with said core, said shell comprising moieties L-X, attached to the core, wherein X is a hydrophilic group and L is a hydrophobic unit.

Preferred latex compositions herein comprise:
(a) an aqueous phase;
(b) from about 5 to about 50% by weight of latex particles dispersed in said aqueous phase, said particles comprising an elastomeric hydrophobic core and an outer hydrophilic shell attached to said core, said core comprising a polymer selected from the group consisting of butadiene, isoprene styrene, and mixtures thereof, and said shell comprising moieties L-X, wherein L comprises a hydrophobic hydrocarbyl group containing one or more unsaturated bonds and X is a hydrophilic group, preferably, polyoxyethylene.

The invention also encompasses a process for preparing a latex composition, which comprises the steps of:
(A) providing a mixture containing
  (a) water;
  (b) a dispersion of from about 5 to about 50% of a substantially water-insoluble polymerizable component which comprises an elastomer monomer having double bonds (preferably at least 2);
  (c) an effective amount of a water-soluble free-radical polymerization initiator;
  (d) an effective amount of a water-soluble chain transfer agent; and
  (e) an effective amount of an amphiphilic diblock emulsifier LX which comprises an unsaturated hydrophobic moiety L having at least one carbon-carbon double bond and a hydrophilic block X integral with said hydrophobic block; and
(B) heating the mixture to a temperature sufficient to cause emulsion polymerization of the polymerizable component, so as to provide a latex composition comprising latex particles capable of forming an elastomeric film having a substantially permanent hydrophilic surface when the water is removed.

Preferred processes herein are those wherein elastomer monomer (b) is a member selected from the group consisting of butadiene, isoprene, styrene, and mixtures thereof. The diblock emulsifier (e) preferably comprises a polyethyleneoxide derivative of a $C_{10}$-$C_{20}$ unsaturated hydrocarbyl moiety.

The invention also encompasses a process for improving the tactile impression of paper or fabric, comprising contacting said paper or fabric with the composition herein, and drying said paper or fabric. The invention also encompasses paper or fabric articles treated with said compositions.

DISCLOSURE OF THE INVENTION

The present invention relates to latex compositions suitable in various applications requiring surface hydrophilicity. The latex compositions comprise: (1) a liquid phase selected from the group consisting of water, water-miscible solvents and mixtures thereof; and (2) an effective amount of latex particles dispersed in the liquid phase. These particles comprise an elastomeric hydrophobic core and an outer hydrophilic shell integral with the elastomeric core. The hydrophilic shell of the particles ultimately translates into the hydrophilic surface of films formed therefrom, and also advantageously stabilizes the particles as colloids in the liquid phase. The shell comprises hydrophilic moieties -X which are attached to the core via linking group L-. When the liquid phase is removed, the particles form an elastomeric film having a substantially permanent hydrophilic surface.

The latex compositions of the present invention have the desirable property of forming elastomeric films having a hydrophilic surface. This property makes these compositions useful for imparting substantially permanent surface hydrophilicity to various hydrophobic and elastomeric materials including polyethylene and polypropylene sheets and films. These compositions can also be used as hydrophilic elastomeric binder systems in making nonwoven fabrics and paper products. These compositions can be most preferably formed by typical emulsion polymerization processes, in the presence of certain diblock ingredients (L-X).

A. Definitions

As used herein, the term "hydrophilic" refers to materials which are substantially wetted by water.

As used herein, the term "hydrophobic" refers to materials which are substantially non-wetted by water.

As used herein, the term "elastomeric" refers to materials having rubber-like properties in terms of extensibility and elastic recovery. See *Condensed Chemical Dictionary* (9th edition 1977), page 335, which defines the term "elastomer".

As used herein, the term "comprising" means various components can be conjointly employed in the latex compositions of the present invention. Accordingly, the term "comprising" encompasses the more restrictive terms "consisting essentially of" and "consisting of".

All percentages, ratios and proportions herein are by weight, unless otherwise specified.

B. Latex Compositions

The latex compositions of the present invention basically comprise: (1) a liquid phase; and (2) particles dispersed in the liquid phase as a colloidally stable suspension. The liquid phase can be selected from water (aqueous), water-miscible solvents, and mixtures of water with these water-miscible solvents. Suitable water-miscible solvents include $C_1$-$C_3$ alcohols such as methyl alcohol, ethyl alcohol and isopropyl alcohol, ketones such as acetone, and other water-miscible solvents well known, for example, in the paint formulator's art. An aqueous (water) phase is typically preferred for the liquid phase.

The key component of the latex composition is the particulate latex material dispersed in the aqueous phase. These latex particles are generally spherical in shape and are typically monodisperse in size, i.e. the particles sizes fall within a narrow range. These particles can sometimes be as large as several microns or as small as 10 nm. However, because the latex particles are typically formed by emulsion polymerization, these particles tend to be submicron in size. Typically, the particle diameter of these latex particles is in the range of from about 50 to about 100 nm.

The latex particles are comprised of both an elastomeric hydrophobic core with an outer hydrophilic shell which is bound to the elastomeric core. The hydrophilic shell needs to be sufficiently integral with the core that the subsequently formed elastomeric film has a substantially permanent hydrophilic surface.

The elastomeric hydrophobic core is the predominant component of the latex particles by weight. This elastomeric core is based on a polymer formed from a monomer, typically in combination with other comonomers to impart properties such as stiffness, strength, resistance to flowability at elevated temperatures, etc. The polymers which form the elastomeric core usually have glass transition ($T_g$) values of about 35° C. or less. Preferred polymers for elastomeric cores usually have $T_g$ values of about $-10°$ C. or less.

The hydrophilic shell is the primary functional component of the latex particles. This shell has two functions. First, the hydrophilic surface colloidally stabilizes the latex particles in the liquid phase, thereby preventing flocculation. The second and more important function of this shell is to provide the desired surface hydrophilicity of the elastomeric film which forms when the liquid phase is removed.

These latex particles are dispersed in the aqueous phase in an effective amount. What is "an effective amount" of latex particles depends upon the particular use of the latex composition, the manner in which it is formed, and like factors. Latex compositions of the present invention usually comprise up to about 60% by weight latex particles on a solids basis. Typically, the latex particles comprise from about 5% to about 25% by weight of the latex composition on a solids basis. These matters may be adjusted at the discretion of the formulator, depending on the viscosity desired and the intended end-use of the dispersion.

In use, these latex particles form an elastomeric film having a hydrophilic surface when the liquid phase is removed. The process by which these particles form the elastomeric film is called "sintering". During sintering, the particles coalesce as the liquid phase is removed. These coalesced particles eventually form a continuous film (sinter) which has a substantially uniform hydrophilic exterior surface.

The method by which the surface hydrophilicity of the elastomeric film can be measured is in terms of its "contact angle". In measuring contact angles, the film is cast on a hard, nonporous material such as glass. A drop of water is then placed on the cast film. The arc inside the water droplet which is measured from the surface of the film to exterior surface of the droplet is called the contact angle. Generally, the more the droplet spreads over (wets) the surface of the film, the lower will be the contact angle, and hence the greater the hydrophilicity of the film. For compositions of the present invention, the contact angle is usually about 30° or less. For preferred latex compositions herein, the contact angle is about 15° or less. A typical method by which the contact angle of elastomeric films of the present invention is measured is described hereinbelow.

A detailed description of the preparation of the latexes herein follows. In general, the preparation comprises an emulsion polymerization process whereby polymerizable monomers such as styrene, butadiene, divinylbenzene, or the like, or mixtures thereof, are polymerized in the presence of diblock co-oligomer ingredient (L-X). The diblock co-oligomer ingredient comprises a tail group (L) which becomes involved in the polymerization reaction, and a head group (X) which has hydrophilic characteristics. For example, the tail group can contain unsaturated bonds, e.g., an oleyl group: and the hydrophilic head can be a group such as polyoxyethylene. During the polymerization reaction a portion of the diblock is linked into the rubbery emulsion particles by its tail group, and the hydrophilic heads become arrayed on the surfaces of the emulsion particles, thereby rendering what would normally be substantially hydrophobic rubbery emulsion particles into particles whose surfaces are hydrophilic.

This emulsion can then be applied onto any desired substrate, to which the emulsion particles adhere and coalesce to provide a coating which is hydrophilic by virtue of the presence of the hydrophilic heads of the diblock ingredient.

PREPARATION AND CHARACTERIZATION OF "SHEL"

(Surface Hydrophilic Elastomeric Latex)

A highly preferred method for preparing the latex compositions of the present invention is by emulsion polymerization. In emulsion polymerization, a diblock material is dispersed in water. A water-soluble free-radical initiator is then added and optionally a water-soluble chain transfer agent is also added to control the molecular weight of the elastomeric particles formed during emulsion polymerization. A polymerizable component containing elastomer monomer, plus any comonomer, is added and the mixture is then heated to a temperature suitable for emulsion polymerization.

During emulsion polymerization, the diblock material acts as an emulsifier, which helps stabilize the monomer droplets of the polymerizable component dispersed in the aqueous phase and forms micelles which become swollen with monomer(s) from the dispersed droplets. (Additional, non-participating emulsifiers may also be added but these do not generally become bound to the latex particles.) While not intending to be limited by theory, it seems that the free-radical initiator diffuses into the monomer-swollen micelles and initiates polymerization of the monomer(s) to form the latex particles. The amphiphilic diblock emulsifier on the surface of the micelles solvates additional monomer and stabilizes the forming latex particles. Eventually, the amphiphilic diblock emulsifier becomes grafted or embedded onto the elastomeric core of the particles to form the hydrophilic surface.

A variety of elastomer monomers can comprise the polymerizable component. The only requirements are that the monomer be substantially water-insoluble and have at least one reactive double bond. Examples of suitable elastomer monomers include butadiene, isoprene, and mixtures thereof. The polymerizable component can also include other comonomers or mixtures of comonomers which impart stiffness and strength, crosslinking capability or other desirable properties to the latex particles. Examples of such comonomers include styrene, alpha-methyl styrene, vinyl toluenes, divinylbenzene, vinyl acetate, acrylic acid, methacrylic acid, acrylonitrile, methacrylonitrile, acrylamide, methacrylamide, methyl acrylate, ethyl acrylate and like acrylates, methyl methacrylate, ethyl methacrylate and like methacrylates, maleic anhydride, fumaric acid, itaconic acid, crotonoic acid, ethylene, propylene, and mixtures thereof.

Usually, the polymerizable component comprises from about 5 to about 50% by weight of the aqueous (water) phase. Preferably, the polymerizable component comprises from about 10 to about 25% by weight of the aqueous phase. The elastomer monomer(s) usually comprises from about 40 to 100% by weight of the polymerizable component, while the comonomer(s) comprises from 0 to about 60% by weight of the component. Preferably, the elastomer monomer(s) comprises from about 60 to 100% by weight of the component, while the comonomer(s) comprise from 0 to about 40% by weight of the component. Particularly preferred polymerizable components comprise from about 50 to about 75% by weight butadiene or isoprene and from about 25 to about 50% by weight styrene or a mixture of styrene with up to about 2% by weight divinylbenzene. Such butadiene-styrene or isoprene-styrene mixtures can optionally comprise up to about 10% by weight acrylic acid or methacrylic acid.

A particularly important component in the emulsion polymerization process of the present invention is the amphiphilic diblock co-oligomer emulsifier. The diblock emulsifier is used in an effective amount in the emulsion polymerization process. What is "an effective amount" depends upon the particular emulsifier being used, the type of latex composition desired, and like factors. Usually, the diblock emulsifier comprises from about 2 to about 20% by weight of the polymerizable component. Preferably, the emulsifier comprises from about 4 to about 10% by weight of the polymerizable component.

Two particularly important factors in determining what amphiphilic diblock emulsifier to use are: (1) the ability of the emulsifier to stabilize the monomer droplets of the polymerizable component in the aqueous phase; and (2) the ability of the emulsifier to become affixed, grafted or otherwise firmly attached onto the core of the formed latex particles. As long as these two key criteria are satisfied, the selection of the diblock emulsifier is essentially a matter of what properties are desired in the latex composition. This diblock emulsifier basically has the structure:

L-X wherein L is the hydrophobic block and X is the hydrophilic block integral with the hydrophobic block.

As exemplification, and not by way of limitation, tail group (L) can be an unsaturated hydrocarbyl group having one or more double bonds. Typically, such unsaturated hydrocarbyl groups will have from about 10 to about 22 carbon atoms and include, for example, hydrocarbyl groups derivable from materials such as oleic acid, linoleic acid, linolenic acid, eleostearic acid, parinaric acid and the like. Other unsaturated L-groups include oligomeric and polymeric materials having residual double bonds, including polybutadiene mixtures, polyisoprene mixtures, and the like. The oleyl group is a preferred L group in the diblock materials used herein.

The hydrophilic head group (X) of the diblock material can be any desired hydrophilic group, including groups such as sulfate, carboxylate, amide, amidate, phosphate, alkoxy, hydroxy, and the like. Highly preferred herein as group X are polyoxyalkylene hydrophilic groups, especially polyoxyethylene groups of the formula $(OCH_2CH_2)_n$—OH where n is an integer from about 5 to about 50, preferably from about 10 to about 20.

It will be readily appreciated by those skilled in the emulsifier arts that the preferred diblock materials for use herein fall within the class of well-known ethoxylated alcohol nonionic surfactants having a hydrocarbyl tail group and an ethoxylated head group, with the proviso that the tail group have one or more points of unsaturation which allow the group to become involved in the polymerization process, thereby bonding the material to the latex particles.

The following examples illustrate the practice of this invention.

EXAMPLE I

A surface-hydrophilic elastomer latex based on styrene-butadiene rubber was prepared in the following manner. A mixture of a surfactant solution prepared by dissolving 0.28 g of oleyl ethoxylate having approximately 20 ethoxylate units ("VOLPO-20") in 20 mL of distilled water, an initiator solution prepared by dissolving 0.035 g of potassium persulfate in 20 mL of distilled water, and an additional 16.4 mL of distilled water were placed in a 250 mL thick-walled glass reaction bottle with a magnetic stirring rod. The distilled water used in this reaction was purged with argon for 15 minutes before being used. The reaction bottle containing the solution mixture of surfactant and initiator was purged with argon for 20 minutes and sealed with a rubber gasket which was covered with a metal bottle cap with two holes. The transfer of 1.75 g of styrene into the reaction bottle was made by injecting the monomers through the rubber gasket using a syringe. In a similar manner, the transfer of 5.25 g of 1,3-butadiene was made by condensing it first in a 15 mL graduated cylinder submerged in dry ice and injecting the condensate into the reaction bottle with a syringe. The reaction bottle was then placed in an oil bath set at 60° C. throughout the reaction period with slow agitation of the reaction mixture with a magnetic stirrer for 16 hours to complete the emulsion polymerization.

Approximately 2 mL of the latex product was dried in an oven at 110° C. for at least one hour. From the weight before and after the drying, the solid content of the latex was estimated to be 9.5%. The surface hydrophilicity of the solid product made from the latex was measured in the following manner. A solid film sample of the latex was obtained by placing 1.0 mL of the reaction product onto a 7.5 cm×7.5 cm glass plate and allowing it to dry at room temperature for several days. The surface hydrophilicity of the film was determined by placing 4 μL of distilled water over the film which was kept horizontal and observing the contact angle between the film surface and water sessile drop using a horizontal microscope equipped with a goniometer.

The contact angle of water averaged over six measurements was 6.3±0.8°.

EXAMPLE II

A surface-hydrophilic elastomer latex based on styrene-butadiene-acrylic acid copolymer was prepared in the following manner. A mixture of a surfactant solution prepared by dissolving 0.32 g of oleyl ethoxylate having approximately 20 ethoxylate units in 15 mL of distilled water, an initiator solution prepared by dissolving 0.142 g of potassium persulfate in 15 mL of distilled water, and additional 26.4 mL of distilled water were placed in a 250-mL thick-walled glass reaction bottle with a magnetic stirring rod. The distilled water used in this reaction was purged with argon for 15 minutes before being used. The reaction bottle containing the solution mixture of surfactant and initiator was purged with argon for 30 minutes and sealed with a rubber gasket and a metal bottle cap with two holes. The transfer of 0.07 g of divinylbenzene, 0.526 g of acrylic acid, and 1.75 g of styrene into the reaction bottle was made by injecting through the rubber gasket with a syringe. The transfer of 5.25 g of 1,3-butadiene was made by condensing it first in a 12 mL graduated cylinder submerged in dry ice and injecting the condensate into the reaction bottle with a syringe. The reaction bottle was then placed in an oil bath set at 60° C. throughout the reaction period with slow agitation of the reaction mixture with a magnetic stirrer for 16 hours to complete the emulsion polymerization. Thus a latex having solid content of 7.1% by weight, which was measured by the method described in Example I, was obtained.

The surface hydrophilicity of the solid film made from the latex was measured by the method described in Example I. The average contact angle of a sessile water drop placed on the surface of a film prepared from the latex was 24±2°.

EXAMPLE III

A surface-hydrophilic elastomer latex containing butadiene-ethylene oxide diblock co-oligomer was prepared in the following manner. A 250 mL round bottom flask was flushed with nitrogen for 30 minutes and then submerged in a dry ice-acetone bath. The transfer of 3.1 g of liquid 1,3-butadiene to the reaction vessel was made after it had been condensed in a 25 mL flask containing calcium hydride and stirred for 3 hours. A solution prepared from 0.033 g of butadiene-ethylene oxide diblock co-oligomer, which had an average molecular weight of 1,845 measured by vapor-phase osmometry and molecular-weight ratio of 2.85 between the ethylene oxide oligomeric segment and butadiene oligomeric segment, dissolved in 15 mL of distilled water, one mL of 1-dodecanemercaptan, an initiator solution prepared by dissolving 0.096 g of potassium persulfate dissolved in 10 mL of distilled water, and additional 5 mL of distilled water were added to the reaction vessel. The water used in this work was freshly distilled just before being used. The flask containing the reaction mixture was sealed, removed from the dry ice-acetone bath, and allowed to warm up until the contents of the flask were melted. The reaction vessel was then heated in an oil bath to about 53° C. and maintained at constant temperature with slow agitation using a magnetic stirrer for 64 hours to complete the emulsion polymerization.

The surface hydrophilicity of the solid film made from the latex was measured by the method described in Example I. The average contact angle of a sessile water drop placed on the surface of a film prepared from the latex was 5.8°.

EXAMPLE IV

A surface-hydrophilic elastomer latex which, even after extensive dialysis, was capable of producing rubbery films having a hydrophilic surface was prepared in the following manner. A 500 mL round bottom flash was flushed with nitrogen gas for 15 minutes and then cooled by submerging in a dry ice-acetone bath. A mixture of 15 g of condensed 1,3-butadiene, 5 g of styrene, 0.4 g of 1-dodecanethiol, a surfactant solution prepared by dissolving 0.8 g of oleyl ethoxylate having approximately 20 ethoxylate units in 40 mL of distilled water, an initiator solution prepared by dissolving 0.4 g of potassium persulfate in 40 mL of distilled water, and an additional 100 mL of distilled water was placed in the reaction vessel. The distilled water used in this reaction was purged with argon for 15 minutes before being used. The flask containing the reaction mixture was sealed, removed from the dry ice-acetone bath, and allowed to warm up until the contents of flask were melted. The reaction vessel was submerged in an oil bath set at 65° C. for 20 hours to complete the emulsion polymerization. A latex having a solid content of 10.5% was obtained.

The surface hydrophilicity of the solid films made from the latex was measured by the method described in Example I. In order to minimize the effect of the possible presence of free surfactant on the surface hydrophilicity of solid product made from the latex, extensive dialysis was applied to the latex by placing about 20 milliliters of latex in a dialysis membrane tube immersed in a large amount of water which was periodically changed. The average contact angles of sessile water drops placed on the surface of solid films prepared from the latex aliquots after various dialysis periods are given in Table I.

TABLE I

| Effect of latex dialysis on surface hydrophilicity | |
|---|---|
| Dialysis Period (hours) | Contact Angle (degrees) |
| 0 | 6.5 |
| 4 | 5.5 |
| 24 | 5.5 |
| 49 | 5.3 |
| 73 | 6.3 |

EXAMPLE V

A latex capable of producing rubbery films which could maintain stable hydrophilic surface for many weeks in air was prepared in the manner similar to that described in Example IV. The surface hydrophilicity of the solid films made from the latex was measured by the method described in Example I. The average contact angles of sessile water drops placed on the surface of solid films which were aged by exposing in air at the room temperature for various periods of time are given in Table II.

TABLE II

| Effect of aging in air on surface hydrophilicity | |
|---|---|
| Aging Period (days) | Contact Angle (degrees) |
| 2 | 5.7 |
| 4 | 11.3 |

TABLE II-continued

| Effect of aging in air on surface hydrophilicity | |
|---|---|
| Aging Period (days) | Contact Angle (degrees) |
| 7 | 7.5 |
| 9 | 5.8 |
| 17 | 6.0 |
| 62 | 9.0 |

EXAMPLE VI

A surface-hydrophilic elastomer latex capable of producing rubbery films, which could maintain stable hydrophilic surface even after being washed with water for many hours, was prepared in the following manner. A mixture of 2.5 g of 1,3-butadlene, 2.5 g of styrene, 0.0845 g of 1-dodecanethiol, 0.2 g of oleyl ethoxylate having approximately 20 ethoxylate units, 0.1 g of potassium persulfate, and 45 mL of distilled and argon-purged water was placed in a 250-mL flask, and emulsion polymerization was carried out as described in Example IV. A latex having a solid content of 10.7% was obtained.

The surface hydrophilicity of the solid films made from the latex was measured by the method described in Example I. The average contact angles of sessile water drops placed on the surface of solid films which were washed continuously for different lengths of time in a large amount of distilled water, rinsed under running water, and dried thoroughly are listed in Table III.

TABLE III

| Effect of washing | |
|---|---|
| Washing Period (days) | Contact Angle (degrees) |
| 0 | 6.1 |
| 20 | 9.3 |
| 40 | 13.5 |
| 60 | 13.2 |

As can be seen from the foregoing Examples, the emulsion polymerization process used herein employs reaction conditions typical of the art, with the major exception that the participating diblock material is present in the reaction mixture. Generally, a temperature of about 50° C. is sufficient to emulsion polymerization of the polymerizable component at a reasonable rate. Such temperatures also ensure that the amphiphilic diblock emulsifier is incorporated into the elastomeric particles without the need of any additional cross-linking monomer such as divinylbenzene. Typically, the temperature used for emulsion polymerization ranges from about 60° C. to about 65° C. Emulsion polymerization is carried out for a sufficient time to ensure formation of the latex composition; e.g. from about 8 to about 64 hours. While emulsion polymerization as described herein forms aqueous latex compositions, latexes involving other water-miscible solvents as the liquid phase can be formed by solvent exchange.

Optionally, initiators other than those exemplified may be used, but such matters are within the knowledge of those skilled in the latex polymerization art and need not be described in detail, herein.

Another, but less preferred, method for preparing latex compositions of the present invention is by surface grafting an amphiphilic diblock material onto elastomeric particles present in a preformed latex. Such preformed latexes are commercially available or else can be synthesized by standard emulsion polymerization techniques. See U.S. Pat. No. 3,397,165 to Goodman et al, issued Aug. 13, 1968, which discloses the preparation of an aqueous latex of butadiene polymer by emulsion polymerization using a seed latex. See also U.S. Pat. No. 3,575,913 to Meier, issued Apr. 20, 1971, which discloses the preparation of latexes such as those formed by polymerizing itaconic acid, styrene and butadiene by the "shot growth" technique.

Suitable amphiphilic diblock materials include those previously defined for use in the emulsion polymerization process for making latex compositions of the present invention. Typically, the diblock material is used in an amount of from about 2 to about 20% by weight of the preformed latex.

In order to cause surface grafting of the amphiphilic diblock onto the latex particles of the preformed latex, a free-radical initiator is used. Suitable free-radical initiators can be water-soluble or oil-soluble. Representative examples of oil-soluble free-radical initiators include azobisisobutyronitrile (AIBN), dimethyl azobisisobutyronitrile,1,4-diazobiscyclo(2.2.2) octane, and the like. The free-radical initiator is used in an amount effective to cause surface grafting of the amphiphilic diblock material onto the elastomeric particles present in the preformed latex, e.g. from about 0.1 to about 1% by weight of latex solids.

Surface grafting of the amphiphilic diblock material onto the latex particles of the preformed latex is typically carried out at a temperature of at least about 50° C. Preferred temperatures for surface grafting are from about 60° to about 65° C. The mixture of preformed latex, amphiphilic diblock material and free-radical initiator is heated to the appropriate temperature for a period of time sufficient to ensure surface grafting of the amphiphilic diblock material onto the latex particles of the preformed latex. Aqueous latex compositions formed by surface grafting can be converted to water-miscible solvent (alcohol) latexes by solvent exchange techniques.

The following Examples illustrate grafting technique and the use of the hydrophilic latexes of this invention to coat an otherwise hydrophobic apertured sheet material to render its surface hydrophilic.

EXAMPLE VII

The preparation of a surface-hydrophilic elastomer latex by attaching an amphiphilic diblock co-oligomer surfactant onto the surface of preformed styrene-butadiene rubber latex was carried out in the following manner.

A styrene-butadiene rubber latex was prepared first. A comonomer mixture consisting of 15 g of condensed 1,3-butadiene and 5 g of styrene was dispersed and polymerized in 180 mL of distilled water with 2.8 g of sodium lauryl sulfate emulsifier, 0.4 g of potassium persulfate initiator, and 0.4 g of 1-dodecanol chain transfer agent. A latex having a solid content of 11.0% was obtained. The surface hydrophilicity of the solid film made from the latex was measured by the method described in Example I. The average contact angle of a sessile water drop placed on the surface of a film prepared from the latex was 77.5±4.0°.

The preformed styrene-butadiene latex described above, which produced hydrophobic films, was converted to a surface-hydrophilic elastomer latex by the following procedure. A mixture of 0.22 g of oleyl ethoxylate having approximately 20 ethoxylate units and 0.044 g of potassium persulfate in 3.6 g of ethanol was added to 20 g of the preformed latex. The reaction bottle containing the mixture was purged with argon for 10 minutes and then sealed with a bottle cap and a rubber septum. The reaction mixture was then placed in an oil bath set at 75° C. with slow agitation for 24 hours to complete the modification reaction of latex.

The surface hydrophilicity of the solid film made from the modified latex was measured by the method described in Example I. The average contact angle of a sessile water drop placed on the surface of a film prepared from the modified latex was 5.3°. The stability of the surface hydrophilicity against water was tested by washing the film prepared from the modified latex with an excess amount of water for 20 hours and subsequent drying. The average sessile contact angle of water droplet placed on the extensively washed film was 6.2°.

The hydrophilic latexes of the present invention have a variety of industrial uses. For example, they may be used to coat otherwise hydrophobic materials to render them "surface-hydrophilic". Example VIII illustrates this use.

EXAMPLE VIII

A perforated polyethylene film having numerous (approximately $100/cm^2$) small holes with less than 1 mm diameter is treated with a surface-hydrophilic elastomer latex capable of forming films having a hydrophilic surface. One side of a 4"×4" sample piece of perforated polyethylene (Mullane and Smith U.S. Pat. No. 4,324,246 incorporated herein by reference) is coated with 1 mL surface-hydrophilic elastomer latex of Example I diluted with 4 mL of distilled water by spraying. The latex-covered sample is allowed to dry at 23° C. for 24 hours to form a single-side wettable perforated film. The single-side wettability of the sample is tested in the following manner. The sample is placed on a piece of absorbent material, such as paper towel, with the latex-treated side facing down toward the absorbent. A small droplet of water is placed on the untreated side of the sample. Upon application of a gentle mechanical perturbation, the water droplet quickly disappears from the untreated side by being transferred to the latex-treated side of the sample and eventually to the absorbent material. No observable trace of water is left on the untreated side.

A similar experiment is carried out by using a perforated polyethylene film without any latex treatment. A water droplet placed on top of the surface of the untreated perforated film remains at the initial position without being transferred to the other side facing down on the absorbent nor spread over the top side. Application of mechanical perturbation similar to or greater than that used in the previous experiment does not induce the fluid to transfer across the perforated film.

Another experiment is carried out by using a perforated polyethylene sample similar to the first experiment with one side being treated with a surface-hydrophilic elastomer latex. This time, however, the latex-treated side of the perforated film is facing up and the untreated side was facing down toward an absorbent. A water droplet placed on the sample immediately spreads over the top surface treated with the latex. The transfer of the water to the other side across the perforation is not observed. The surface of the perforated film facing the absorbent material remains dry, while the top side is wet.

The surface-hydrophilic sheet of Example VIII is useful as the topsheet of a diaper, bandage, catamenial, or the like, and reduces the re-wet problem that is commonly associated with such absorbent products.

EXAMPLE IX

The compositions herein can be applied to paper or to fabrics to yield products having a soft, silky "feel", but which retain their wet strength.

In a typical mode, a latex emulsion of Example II is sprayed evenly onto a sheet of ordinary writing paper until the paper is thoroughly soaked. After air-drying, the paper has a softer feel.

In an alternate mode, a latex emulsion of Example I is thoroughly admixed with a slurry of comminuted cellulose pulp and converted to standard facial tissue. The wet-strength and feel of the tissue are thereby improved.

What is claimed is:
1. A latex composition which comprises:
   (a) a liquid phase selected from the group consisting of water, water-miscible solvents, and mixtures thereof; and
   (b) from about 5 to about 50% by weight of latex particles dispersed in said aqueous phase, said particles comprising an elastomeric hydrophobic core and an outer hydrophilic shell attached to said core, said core comprising a polymer selected from the group consisting of butadiene, isoprene styrene, and mixtures thereof, and said shell comprising moieties L-X, wherein L comprises a hydrophobic hydrocarbyl group containing one or more unsaturated bonds and X is a polyoxyalkylene hydrophilic group.
2. A composition according to claim 1 wherein X is a polyoxyethylene group.

* * * * *